United States Patent
Lee et al.

(10) Patent No.: US 12,137,999 B2
(45) Date of Patent: Nov. 12, 2024

(54) METHODS FOR LAPAROSCOPIC SURGERY WITH ASSIST ROBOT AND CONTROLLING METHODS FOR LAPAROSCOPIC SURGERY SYSTEM WITH ASSIST ROBOT

(71) Applicant: LIVSMED INC., Seongnam-si (KR)

(72) Inventors: Jung Joo Lee, Yongin-si (KR); Hee Jin Kim, Seoul (KR); Dong Kyu Jang, Seoul (KR)

(73) Assignee: Livsmed Inc., Seongnam-si (KR)

( * ) Notice: Subject to any disclaimer, the term of this patent is extended or adjusted under 35 U.S.C. 154(b) by 457 days.

(21) Appl. No.: 17/125,097

(22) Filed: Dec. 17, 2020

(65) Prior Publication Data
US 2022/0061938 A1  Mar. 3, 2022

Related U.S. Application Data

(60) Provisional application No. 63/072,426, filed on Aug. 31, 2020.

(51) Int. Cl.
| | |
|---|---|
| *A61B 34/37* | (2016.01) |
| *A61B 17/00* | (2006.01) |
| *A61B 34/00* | (2016.01) |
| *A61B 34/30* | (2016.01) |
| *A61G 13/00* | (2006.01) |
| *A61G 13/10* | (2006.01) |
| *A61B 90/00* | (2016.01) |

(52) U.S. Cl.
CPC ........ *A61B 34/37* (2016.02); *A61B 17/00234* (2013.01); *A61B 34/25* (2016.02); *A61B 34/74* (2016.02); *A61G 13/101* (2013.01); *A61B 2017/00221* (2013.01); *A61B 2034/302* (2016.02); *A61B 90/37* (2016.02)

(58) Field of Classification Search
CPC ........ A61B 17/00234; A61B 2034/302; A61B 90/37; A61B 2017/00221; A61G 13/101
See application file for complete search history.

(56) References Cited

U.S. PATENT DOCUMENTS

| | | | |
|---|---|---|---|
| 9,788,903 B2 | 10/2017 | Kim et al. | |
| 10,695,141 B2 | 6/2020 | Lee | |
| 10,709,467 B2 | 7/2020 | Lee et al. | |
| 10,722,315 B2 | 7/2020 | Lee et al. | |
| 2017/0189130 A1* | 7/2017 | Weir | A61B 34/37 |
| 2018/0036088 A1* | 2/2018 | Kilroy | A61B 34/74 |
| 2018/0078439 A1* | 3/2018 | Cagle | A61B 34/30 |

(Continued)

*Primary Examiner* — Mallika D Fairchild
*Assistant Examiner* — Thien Jason Tran
(74) *Attorney, Agent, or Firm* — Knobbe, Martens, Olson & Bear, LLP

(57) ABSTRACT

This application relates to methods and systems for laparoscopic surgery with assist robot and controlling methods for laparoscopic surgery system with assist robot. In one aspect, the method includes arranging a control assist robot on one region of a bed and a motion assist robot on another region of the bed to be spaced a certain distance apart from the control assist robot. The motion assist robot includes a surgical instrument that moves according to a control of the control assist robot. The method also includes performing laparoscopic surgery in a state in which an operator is positioned next to the control assist robot and grips a manual type instrument with one hand and the control assist robot with the other hand.

22 Claims, 13 Drawing Sheets

(56) References Cited

U.S. PATENT DOCUMENTS

2018/0200010 A1    7/2018  Hares et al.
2018/0353252 A1   12/2018  Chassot et al.
2020/0397520 A1*  12/2020  Penny .................. A61B 90/361

* cited by examiner

METHODS FOR LAPAROSCOPIC SURGERY WITH ASSIST ROBOT AND CONTROLLING METHODS FOR LAPAROSCOPIC SURGERY SYSTEM WITH ASSIST ROBOT

RELATED APPLICATIONS

This application claims priority to and the benefit of Provisional Application No. 63/072,426 filed on Aug. 31, 2020 in the U.S. Patent and Trademark Office, the entire contents of which are incorporated herein by reference.

BACKGROUND

Technical Field

One or more embodiments relates to a method of performing laparoscopic surgery using an assist robot and a method of controlling a laparoscopic surgery system using the assist robot, and in detail, a method of performing laparoscopic surgery using assist robots including a control assist robot and a motion assist robot and a method of controlling a laparoscopic surgery system using the assist robots.

Description of the Related Technology

Surgery denotes a process of curing illness by cutting, incising, or manipulating the skin, the mucosa layer, and other tissues by using a medical instrument. In addition, laparotomy, etc. that treats, shapes, or removes an organ by cutting and opening the skin of a surgical site may cause bleeding, side effects, the pain of a patient, scar, etc. Therefore, surgery performed by inserting only a medical instrument, e.g., a laparoscope, a surgical instrument, a microscope for microsurgery, etc. after forming a predetermined hole in the skin, or surgery using a robot has been recently considered as an alternative.

A surgical instrument is an instrument having an end tool provided at an end of a shaft that passes through a hole in the skin, so that an operator directly manipulates the end tool with his/her own hands via a predetermined driver or manipulates the end tool by using a robot arm to carry out a surgery on a surgical site. The end tool provided at the surgical instrument performs a pivoting operation, a gripping operation, a cutting operation, etc. through a certain structure.

The information in the background art described above was obtained by the inventors for the purpose of developing the present disclosure or was obtained during the process of developing the present disclosure. As such, it is to be appreciated that this information did not necessarily belong to the public domain before the patent filing date of the present disclosure.

SUMMARY

An embodiment of the present disclosure provides a method of performing laparoscopic surgery using an assist robot and a method of controlling a laparoscopic surgery system using the assist robot, and in detail, a method of performing laparoscopic surgery using assist robots including a control assist robot and a motion assist robot and a method of controlling a laparoscopic surgery system using the assist robots.

An embodiment of the present disclosure provides a method of performing laparoscopic surgery using an assist robot includes: arranging a control assist robot on one region of a bed and a motion assist robot on another region of the bed, wherein the motion assist robot includes a surgical instrument that moves according to a control of the control assist robot; positioning an operator next to the control assist robot; and performing laparoscopic surgery in a state in which the operator grips a manual type instrument with one hand and the control assist robot with the other hand.

One aspect of the present disclosure provides a method of performing a laparoscopic surgery, which may comprise: providing a surgical bed on which a patient is placed, a slave assist robot disposed at or adjacent to a first region of the surgical bed, and a master assist robot disposed at or adjacent a second region of the surgical bed, the second region being apart from the first region; the slave assist robot being configured to move relative to the surgical bed and comprising a base and a robotic arm attached to the base, and the slave assist robot being configured to move at least one laparoscopic surgery instrument attached to the robotic arm, and the master assist robot comprising a control handle configured to control the robotic arm, the master robot and the slave assist robot being electrically connected to communicate each other; and providing a manual laparoscopic surgery tool at the second region of the surgical bed; and performing a combined laparoscopic surgery on the patient by controlling the control handle of the master assist robot with one hand of a surgeon positioned at the second region of the surgical bed while controlling the manual laparoscopic surgery tool with the other hand of the surgeon.

In the foregoing method, the first region and the second region may be located at the same side of the surgical bed. The first region may be located at a first side of the surgical bed and the second region may be located at a second side of the surgical bed that is different from the first side. The first region may be located at a first side of the surgical bed and the second region may be located at a second side of the surgical bed that is opposite to the first side. The first region may be located at a first side of the surgical bed and the second region may be located at a second side of the surgical bed that is adjacent to and crosses the first side the surgical bed.

Still in the foregoing method, the slave assist robot may be separate from the bed and configured to move along at least one side of the surgical bed. The surgical bed may comprise a rail, the slave assist robot may be coupled to the rail, and the slave assist robot may be configured to move along the rail. At least one of the master assist robot and the slave assist robot may be detachably coupled to the respective first or second region of the surgical bed.

Yet in the foregoing method, an additional slave assist robot may be provided at or adjacent the second region of the surgical bed and configured to move an additional laparoscopic surgery instrument attached to a robotic arm of the additional slave assist robot, wherein the laparoscopic surgery instrument and the additional laparoscopic surgery instrument may be different from each other, and wherein the method may further comprise: receiving a user input regarding at least one of a type of the manual laparoscopic surgery tool and a type of the laparoscopic surgery; and automatically selecting one of the laparoscopic surgery instrument and the additional laparoscopic surgery instruction based on the at least one of the type of the manual laparoscopic surgery tool and the type of the laparoscopic surgery.

The foregoing method may further comprise: operating the slave assist robot and the master assist robot in a first operation mode such that when the control handle of the master assist robot moves along a first direction, the robotic arm moves the first laparoscopic surgery instrument along a second direction opposite to the first direction; operating the slave assist robot and the master assist robot in a second operation mode such that when the control handle moves along the first direction, the robotic arm moves the first laparoscopic surgery instrument along the first direction; and switching between the first operation mode and the second operation mode. The foregoing method further comprises automatically setting one of the first operation mode and the second operation mode based on a type of the manual laparoscopic surgery tool.

Another aspect of the present disclosure provides robot-assisted laparoscopic surgery system, which may comprise: a slave assist robot disposed at or adjacent to a first region of a surgical bed that comprises a plurality of sides, the slave assist robot comprising a base and a robotic arm attached to the base and configured to move at least one laparoscopic surgery instrument attached to the robotic arm; and a master assist robot disposed at a second region of the surgical bed and electrically connected to the slave assist robot to communicate with the slave assist robot, the master assist robot comprising a control handle configured to control the slave assist robot to allow a surgeon adjacent to one of the plurality of sides of the surgical bed to manipulate the robotic arm of the slave assist robot by operating the control handle with one hand while the surgeon operates a manual laparoscopic tool with the other hand at the surgical bed.

Still another aspect of the present disclosure provides a robot-assisted laparoscopic surgery system, which may comprise: a slave assist robot comprising a base and a robotic arm attached to the base and configured to move at least one laparoscopic surgery instrument attached to the robotic arm, the base configured to move relative to a surgical bed; and a master assist robot configured to be detachably coupled to the surgical bed and electrically connected to the slave assist robot to communicate with the slave assist robot, the master assist robot comprising a control handle configured to control the slave assist robot to allow a surgeon adjacent to the surgical bed to manipulate the robotic arm of the slave assist robot by operating the control handle with one hand while the surgeon operates a manual laparoscopic tool with the other hand the surgical bed.

Yet another aspect of the present disclosure provides a method of performing laparoscopic surgery using an assist robot, which may comprise: arranging a control assist robot on one region of a bed and a motion assist robot on another region of the bed to be spaced a certain distance apart from the control assist robot, wherein the motion assist robot includes a surgical instrument that moves according to a control of the control assist robot; and performing laparoscopic surgery in a state in which an operator is positioned next to the control assist robot and grips a manual type instrument with one hand and the control assist robot with the other hand.

In the foregoing method, the motion assist robot may be disposed at a location spaced a certain distance apart from the operator and perform a motion at a location where an arm of the operator does not directly reach. The manual instrument may be directly gripped and driven by the operator, and the surgical instrument included in the motion assist robot may be spaced apart from the operator and is remotely controlled. The surgical instrument of the motion assist robot may comprise at least a pivot driving mode and an intuitive driving mode, wherein in the pivot driving mode the surgical instrument of the motion assist robot may move in a direction opposite to a control movement of the control assist robot based on a trocar point of a patient, wherein in the intuitive driving mode the surgical instrument of the motion assist robot may move in a direction the same as the control movement of the control assist robot based on the trocar point of the patient, and wherein the method may further comprise switching between the pivot driving mode and the intuitive driving mode.

Still in the foregoing method, the control assist robot may comprise a single control assist robot, and the motion assist robot may include a plurality of motion assist robot units. The control assist robot may be configured to select one of the plurality of motion assist robot units to be controlled. The control assist robot and the motion assist robot may be attachable to and detachable from the bed.

A further aspect of the present disclosure provides a method of controlling a laparoscopic surgery system using an assist robot, which may comprise: arranging a control assist robot on one region of a bed and a motion assist robot on another region of the bed to be spaced a certain distance apart from the control assist robot, wherein the motion assist robot includes a surgical instrument that moves according to a control of the control assist robot; and performing laparoscopic surgery in a state in which an operator is positioned next to the control assist robot and grips a manual type instrument with one hand and the control assist robot with the other hand.

Other aspects, features, and advantages other than those described above will become apparent from the following drawings, claims, and detailed description of the embodiments.

According to such an embodiment of the present disclosure, the motion assist robot is positioned in a position and direction inaccessible to the operator's arm, and the operator controls the motion assist robot through the control assist robot, thereby enabling a surgery that is impossible in laparoscopic surgery performed only with hands or robots.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
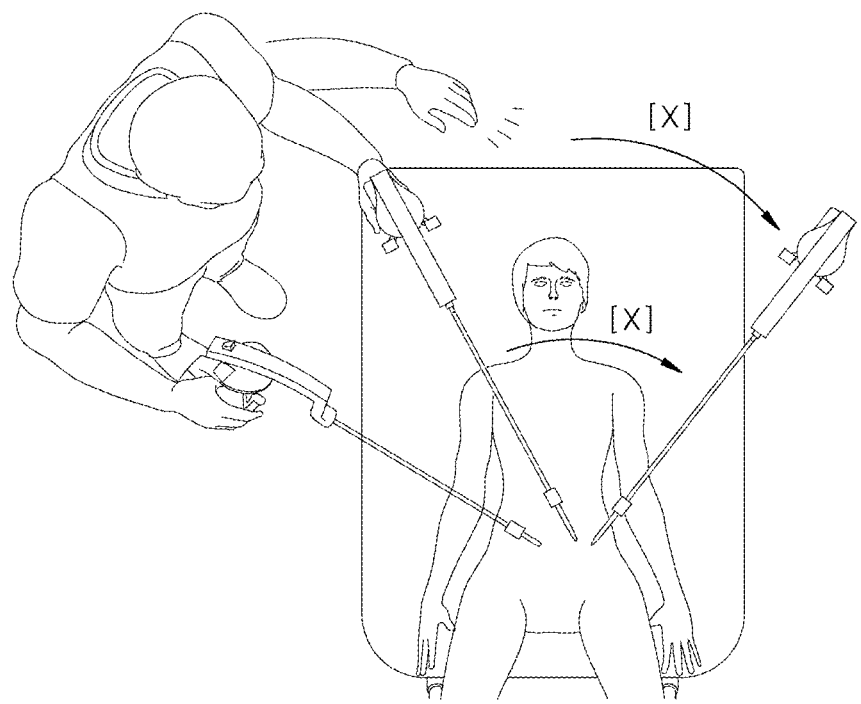
FIG. 1 is a conceptual diagram showing an example of laparoscopic surgery.

As the present disclosure allows for various changes and numerous embodiments, particular embodiments will be illustrated in the drawings and described in detail in the written description. However, this is not intended to limit the present disclosure to particular modes of practice, and it is to be appreciated that all modifications, equivalents, and/or alternatives that do not depart from the spirit and technical scope are encompassed in the disclosure. In the description, certain detailed explanations of the related art are omitted when it is deemed that they may unnecessarily obscure the essence of the present disclosure.

It will be understood that although the terms "first," "second," etc. may be used herein to describe various components, these components should not be limited by these terms. These components are only used to distinguish one component from another. These components are only used to distinguish one component from another.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Hereinafter, the exemplary embodiments will be described in detail with reference to the accompanying drawings. In the drawings, like reference numerals denote like or corresponding elements, and repeated descriptions thereof will be omitted.

Also, it will be understood that various embodiments of the present disclosure may be interpreted or implemented in combination, and technical features of each embodiment may be interpreted or implemented in combination with technical features of other embodiments.

FIG. 1 is an example of laparoscopic surgery and is a conceptual diagram showing the limitations of laparoscopic surgery.

Referring to FIG. 1, in the case of laparotomy, the operator may conveniently access the surgical instrument to the surgical site at a desired position and a desired angle, but there are problems that the patient's wound is large and recovery is slow due to high invasiveness.

Unlike the laparotomy, laparoscopic surgery developed to solve this problems is minimally invasive surgery in which a long and thin surgical instrument is inserted into a small incision hole (approximately 5-12 mm), and may leave minimal wounds and scars to the patient after the surgery due to low invasiveness, so that recovery may be quick, and several side effects of laparotomy may be reduced.

However, the laparoscopic surgery causes inconvenience to the operator, increases the operation time, and is difficult to apply to surgery that requires a complicated surgical operation.

In order to overcome the limitation of laparoscopic surgery, a surgical robot has been developed. A surgical tool of the surgical robot has upper and lower/left and right joints like human hands, and an operator may intuitively manipulate the joints "as if the surgical instrument were his/her hands". As such, inconvenience in operations caused by a straight type laparoscopic surgical instrument which is inserted into a narrow incision hole may be addressed successfully, and complicated surgical operations may be performed for organs located deep inside the abdomen, such as the prostate and pancreas.

In addition, in laparoscopic surgery such as the example shown in FIG. 1, due to the physical limitation in the operator's arm, there are a lot of restrictions in the deployment of the surgical instrument accessing a surgical site. On the other hand, in robot surgery, the surgical instrument may be deployed to access the surgical site in a free position and direction without physical limitations, and through this, various surgical methods that are impossible in the laparoscopic surgery such as the example shown in FIG. 1 have become possible.

However, the surgical robot is limited in distribution due to the high price of 4 billion won per unit, and therefore, 95% of total laparoscopic surgery or greater is still made with the straight type laparoscopic surgical instrument.

Also, in addition to the aspect of costs, because the surgical robot of the related art is of a unilateral (one-sided control) type that is divided into a master robot and a slave robot, a reaction force of the slave robot is not transferred to an operator of the master robot. In addition, because the operator is apart from the patient and located at the master robot side, that is, a non-sterilized area, it is difficult for the operator to immediately deal with an emergency, and thus, an assistant needs to deal with the emergency. Due to these problems, it has been difficult to apply the surgical robot to surgery such as thoracic surgery.

In the case of a method of performing laparoscopic surgery using an assist robot according to an embodiment of the present disclosure, the operator operates next to the patient through the assist robot system consisting of a motion assist robot that operates in a position that is impossible for the operator to operate directly and a virtual control assist robot in a position where the operator may easily operate, but may freely deploy a surgical instrument like the surgical robot, and one operator may control various instruments (including cameras). Through the development of such a laparoscopic surgery system, a paradigm of a new surgical robot providing low cost and safety (that is, surgery is possible right next to the patient) as well as the essential advantages of the surgical robot is proposed. This will be described below in more detail.

Figure 2:
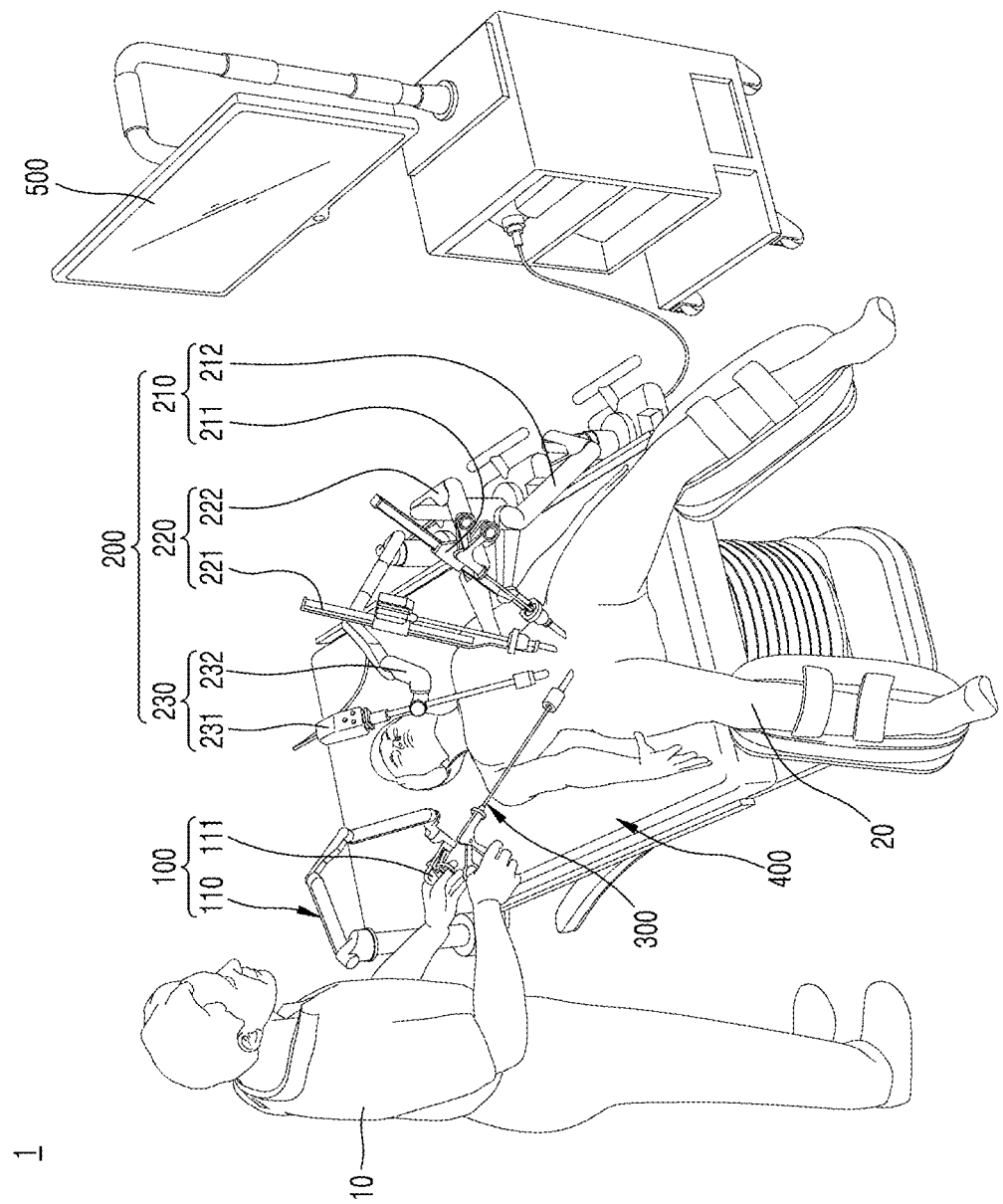
FIG. 2 is a perspective view showing a laparoscopic surgery system in which one operator uses a passive laparoscopic surgical instrument and an assist robot together according to an embodiment of the present disclosure.
Figure 3:
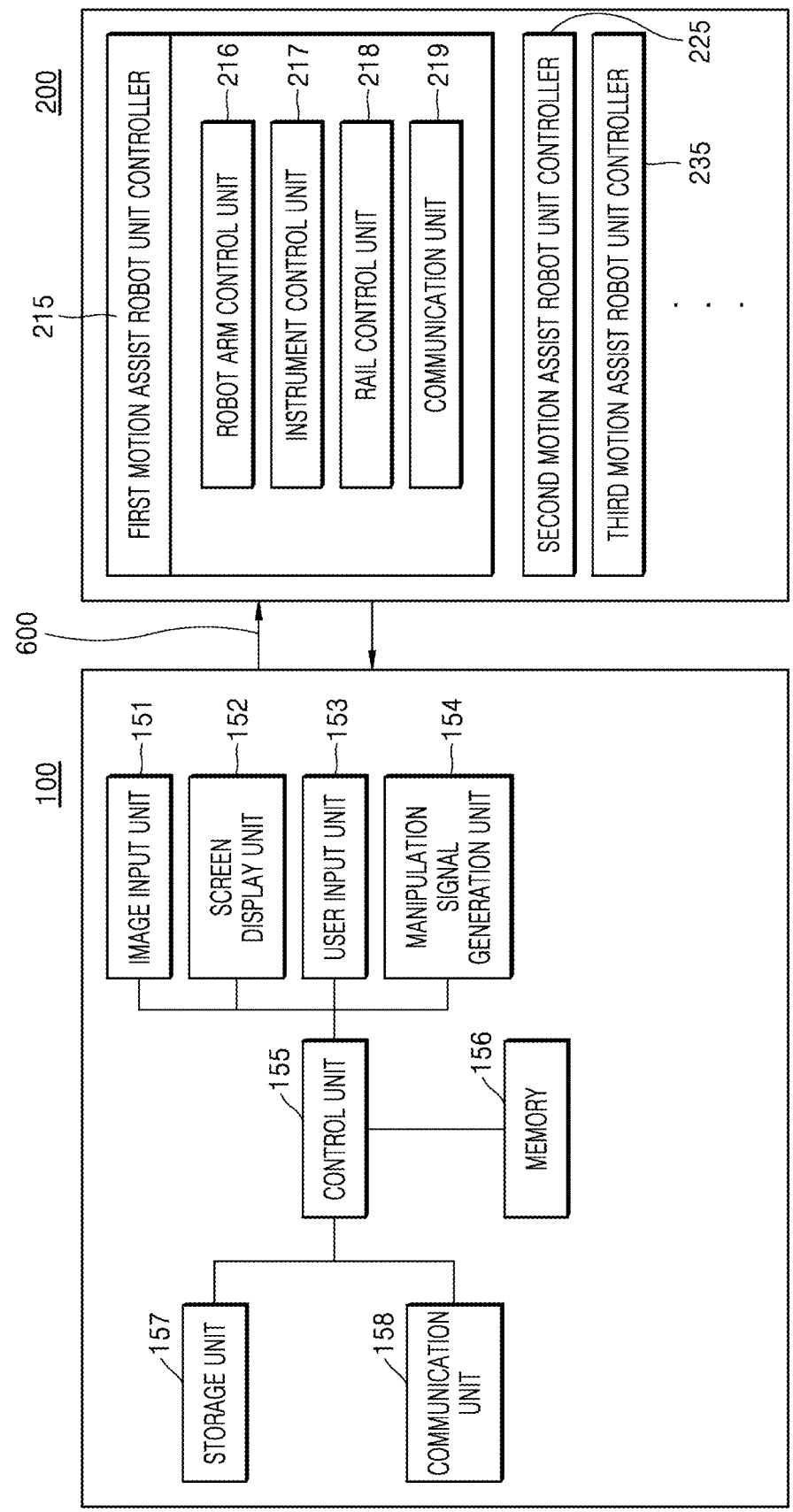
FIG. 3 is a block diagram showing the internal configuration of the laparoscopic surgery system of FIG. 2.
Figure 4:
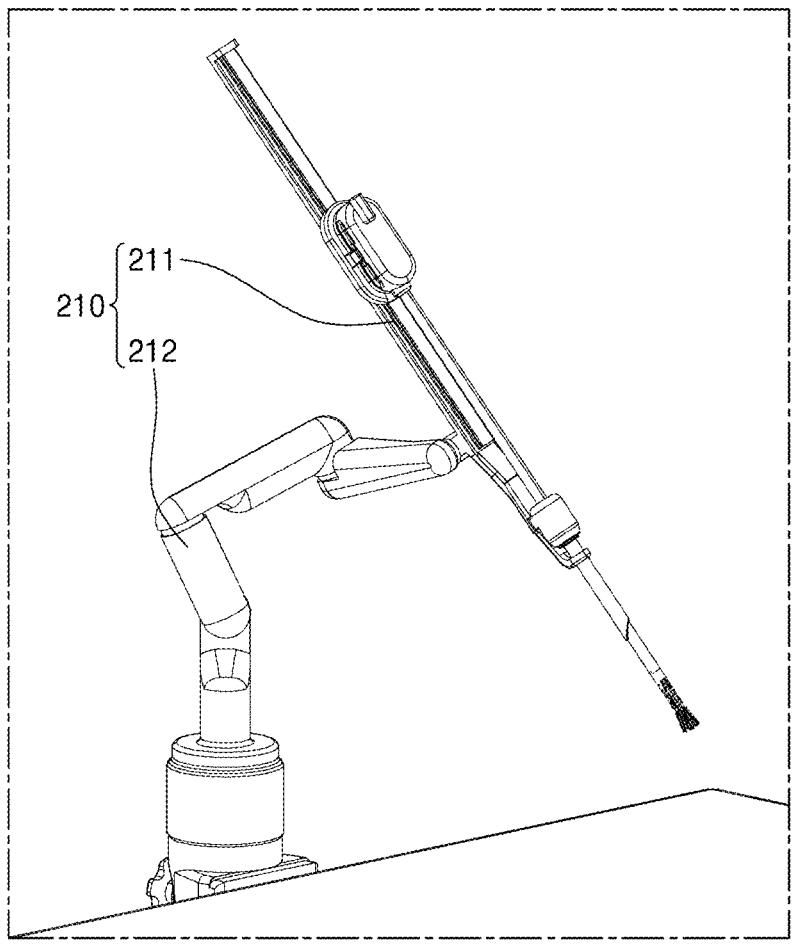
FIG. 4 is a perspective view showing the motion assist robot of the laparoscopic surgery system of FIG. 2.
Figure 5:
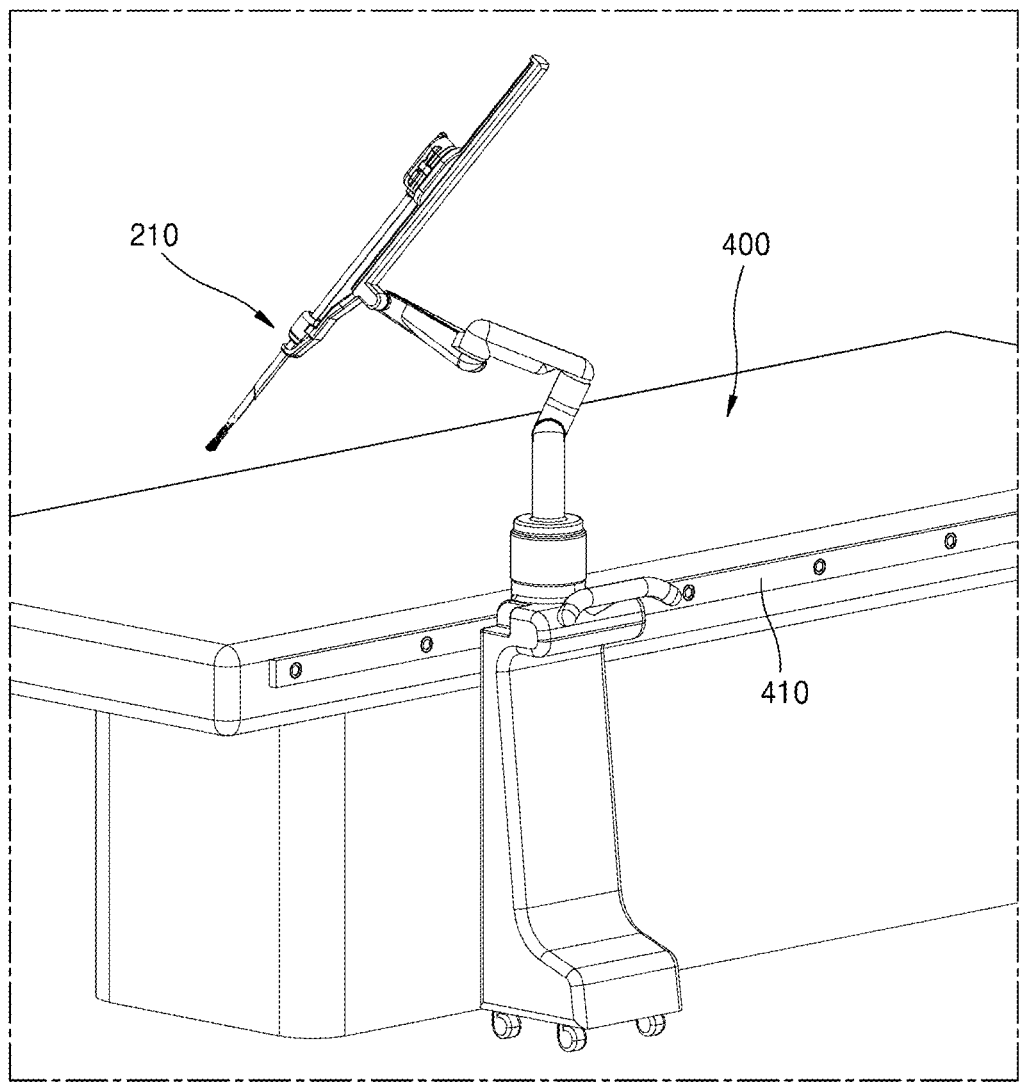
FIG. 5 is a perspective view showing the motion assist robot and the bed of the laparoscopic surgery system of FIG. 2.

FIG. 2 is a perspective view showing a laparoscopic surgery system 1 in which one operator 10 uses a manual type instrument 300 and assist robots 100 and 200 together according to an embodiment of the present disclosure. FIG. 3 is the block diagram showing the internal configuration of the laparoscopic surgery system 1 of FIG. 2. FIG. 4 is a perspective view showing one example 210 of the motion assist robot 200 of the laparoscopic surgery system 1 of FIG. 2. FIG. 5 is a perspective view showing one example 210 of the motion assist robot 200 and the bed 400 of the laparoscopic surgery system 1 of FIG. 2.

First, referring to FIG. 3, the laparoscopic surgery system 1 includes a control assist robot 100 and a motion assist robot 200.

In an embodiment, the control assist robot 100 may include an image input unit 151, a screen display unit 152, a user input unit 153, a manipulation signal generation unit 154, a control unit 155, a memory 156, a storage unit 157, and a communication unit 158 may be included.

The image input unit 151 may receive an image captured by using a camera provided to the laparoscope 231 of the motion assist robot 200 through a wired or wireless communication network.

The screen display unit 152 outputs an image corresponding to the image information received through the image input unit 151 in the form of visual information. In addition, the screen display unit 152 may further output information corresponding to the biometric information when the biometric information about a subject to be treated is input. In addition, the screen display unit 152 may further output image data (e.g., an X-ray image, a CT image, an MRI image, etc.) associated with a patient with respect to a surgical site. Here, the screen display unit 152 may be implemented in the form of, for example, a display member (see 500 in FIG. 2), and an image processing process for outputting the received image information as an image through the screen display unit 152, may be performed by a control unit 155.

In the embodiment illustrated in FIG. 3, the image input unit 151 and the screen display unit 152 are illustrated as included in the control assist robot 100, but embodiments of the present disclosure are not limited thereto. As in the embodiment illustrated in FIG. 2 and the like, the display member 500 may be provided as a separate member spaced from the control assist robot 100. However, embodiments of the present disclosure are not limited thereto, and as shown in FIG. 3 the display member 500 may be provided as a component of the control assist robot 100. In addition, in another embodiment, a plurality of display members 500 are provided, one of which may be disposed adjacent to the control assist robot 100, and others thereof may be disposed spaced apart from the control assist robot 100.

Here, the screen display unit 152 (that is, the display member 500 of FIG. 2) may be provided as a three-dimensional display device. In detail, the three-dimensional display device refers to an image display device in which depth information is added to a two-dimensional image by applying a stereoscopic technique, and this depth information is used to enable an observer to feel a three-dimensional living feeling and a sense of reality. The laparoscopic surgery system 1 according to an embodiment of the present disclosure may provide a more realistic virtual environment to a user by including a three-dimensional display device as a screen display unit 152.

The user input unit 153 is a member for allowing the operator to manipulate the positions and functions of the motion assist robot units 210, 220 and 230 of the motion assist robot 200. The user input unit 153 may be formed in the form of a handle-shaped manipulation member (see 111 in FIG. 2) as illustrated in FIG. 2. However, the shape thereof is not limited thereto, and may vary as long as the same purpose is achieved. In addition, for example, from among user input units, some may be formed in a shape of a handle, and others may be formed in the shape of a clutch button. In some embodiments, a finger insertion tube or insertion tube ring may be further formed so as to allow the operator's finger to be inserted and fixed to facilitate operation of the surgical tool.

When the operator manipulates the user input unit 153 to move the position of motion assist robot units 210, 220 and 230 or manipulate a surgical operation thereof, the manipulation signal generation unit 154 may generate a corresponding manipulation signal, and transmit the same to the motion assist robot 200 through the communication unit 158. The manipulation signal may be transmitted and received through a wired or wireless communication network.

The control unit 155 is a kind of central processing unit and controls the operation of each component so that the above-described functions can be performed. For example, the control unit 155 may perform the function of converting an image that has been input through the image input unit 151 into an image that is to be displayed through the screen display unit 152.

The memory 156 may perform the function of temporarily or permanently storing data processed by the control unit 155. Here, the memory 156 may include a magnetic storage medium or a flash storage medium, but the scope of the present disclosure is not limited thereto.

The storage unit 157 may store data received from the motion assist robot 200. In addition, the storage unit 157 may store various input data (e.g., patient data, device data, surgery data, etc.).

The communication unit 158 interworks with a communication network 600 to provide a communication interface for transmitting and receiving image data transmitted from the motion assist robot 200 and control data transmitted from the control assist robot 100.

The motion assist robot 200 may include a plurality of motion assist robot unit controllers 215, 225, and 235. Further, the motion assist robot unit controller 215 includes a robot arm control unit 216, an instrument control unit 217, and a communication unit 219. In addition, the motion assist robot unit controller 215 may further include a rail control unit 218.

The robot arm control unit 216 may receive a manipulation signal generated by the manipulation signal generation unit 154 of the control assist robot 100 and control the robot arm 212 to operate according to the manipulation signal.

The instrument control unit 217 may receive a manipulation signal generated by the manipulation signal generation unit 154 of the control assist robot 100 and control the surgical instrument 211 to operate according to the manipulation signal.

The rail control unit 218 may receive a manipulation signal generated by the manipulation signal generation unit 154 of the control assist robot 100, and controls the motion assist robot unit 210 to move along the rail 410 of the bed 400 according to the manipulation signal.

The communication unit 219 interworks with the communication network 600 to provide a communication interface for transmitting and receiving image data transmitted from the motion assist robot 200 and control data transmitted from the control assist robot 100.

Meanwhile, the communication network 600 connects the control assist robot 100 to the motion assist robot 200. That is, the communication network 600 refers to a communication network that provides an access path so that data can be transmitted/received between the control assist robot 100 and the motion assist robot 20 after the control assist robot 100 and the motion assist robot 200 are connected to each other. The communication network 600 may be, for example, a wired network such as local area networks (LANs), wired area networks (WANs), metropolitan area networks (MANs), integrated service digital networks (IS- DNs), or wireless LANs, CDMA, Bluetooth, satellite communication, etc. However, the scope of present disclosure is not limited thereto.

Referring to FIGS. 2 to 5, a laparoscopic surgery system 1 according to an embodiment of the present disclosure includes a control assist robot 100, a motion assist robot 200, a manual type instrument 300, and a bed 400.

In the laparoscopic surgery system 1 according to an embodiment of the present disclosure, the control assist robot 100 serves as a master robot for the motion assist robot 200, and the motion assist robot 200 serves as a slave robot for the control assist robot 100. When the operator manipulates a control member (e.g., a handle) provided in the control assist robot 100, a surgical instrument coupled to the robot arm of the motion assist robot 200 or gripped by the robot arm is manipulated to perform surgery.

For example, the control assist robot 100 is disposed on one side of the bed 400 and serves to manipulate one or more of the motion assist robots 200. In an embodiment, the control assist robot 100 and the motion assist robot 200 may face each other with the bed 400 located therebetween. In an embodiment, the control assist robot 100 may be disposed on one side (e.g., a longer direction) of the bed 400, and the motion assist robot 200 may be disposed on another side (e.g., a shorter direction) of the bed 400, which is not the opposite direction. In an embodiment, the control assist robot 100 and the motion assist robot 200 may be located in different areas on the same side (e.g., a longer direction) of the bed 400.

In an embodiment, as shown in FIG. 2, the control assist robot 100 may be located on the left side of the operator 10, and the operator 10 manipulates the control assist robot 100 with the left hand, and the manual type instrument 300 with the right hand. In an embodiment, the control assist robot 100 may be located on the right side of the operator 10, and the operator 10 may operate the control assist robot 100 with the right hand and the manual type instrument 300 with the left hand. In addition, in the embodiment of FIG. 2, the control assist robot 100 is located on the right side of the bed 400 or the patient 20, and the motion assist robot 200 is located on the left side of the bed 400 or a patient 20, but other configurations are possible. In an embodiment, the control assist robot 100 may be located on the left side of the bed 400 or the patient 20, and the motion assist robot 200 may be located on the right side of the bed 400 or the patient 20. In this embodiment, the display 500 may be located on the right side of the bed 400 or the patient 20.

As an embodiment, the control assist robot 100 may be formed to have 7 or more degrees of freedom to manipulate the motion assist robot 200. Here, the control assist robot 100 is formed to be attachable to/detachable from the bed 400 and may be arranged near the location where the operator performs surgery. In an embodiment, regarding the control assist robot 100, a base part thereof may not move while the control assist robot 100 is attached on the bed 400, or, along the side of the bed 400 on which the control assist robot 100 is attached (e.g. a longer direction), the base part may move closer to or away from the operator. When the control assist robot 100 moves along the bed 400, the movement may be made through rails, etc.

In an embodiment, the control assist robot 100 may be located near the bed 400 without being directly attached to the bed 400, as long as the control assist robot 100 is located near the location where the operator performs surgery. In the present embodiment, there may be a support for supporting the control assist robot 100 upwards. The support may include wheels or the like so as to move automatically or manually. Various locations of the control assist robot 100 will be described later with reference to FIG. 7, etc.

The control assist robot 100 includes a manipulation member 111, which can also be referred to as a control member, and an arm 110 supporting the same so that it may be manipulated by one hand of the operator. The manipulation member 111 may control at least one of the robot arms 212, 222 and 232 attached to the motion assist robot 200 while being moved directly by one hand of the operator 10. In this case, the operator 10 may operate the manual laparoscopic surgical instrument 300 with the other hand. In an embodiment, two hands of the operator 10 may move simultaneously, so that the time for manual laparoscopic surgery and the time for laparoscopic surgery that is operated by a robot may overlap completely and may be performed simultaneously. That is, the surgery may be performed while the movement of both hands of the operator is implemented in real-time with each of the manual type instrument 300 and the motion assist robot 200. In another embodiment, although the operator 10 moves both hands together during laparoscopic surgery, the time for manual laparoscopic surgery and the time for laparoscopic surgery that is operated by a robot may overlap partially. In another embodiment, although the operator 10 moves both hands together during laparoscopic surgery, the time for manual laparoscopic surgery and the time for laparoscopic surgery that is operated by a robot may not overlap and the manual laparoscopic surgery and the robot-driving laparoscopic surgery may be sequentially performed.

For example, during laparoscopic surgery, the manual laparoscopic surgical instrument operation performed with the right hand and the control assist robot operation performed with the left hand may be alternately performed. In this case, in an embodiment, the time for right-hand manipulation and the time for left-hand manipulation may overlap partially and the both hands may be alternately used to perform the manipulation to perform surgery. In an embodiment, the right-hand manipulation and the left-hand manipulation may be alternately performed such that the left-hand manipulation does not occur while the right-hand manipulation is performed, whereas the right-hand manipulation does not occur while the left-hand manipulation is performed.

The manipulation member 111 may be implemented as one or more handles as illustrated in FIG. 2, and a manipulation signal according to the manipulate of the operator 10 is transmitted to the motion assist robot 200 through a wired or wireless communication network, and the motion assist robot unit 210 is controlled. That is, when the operator 10 manipulates the manipulation member 111, a control signal is transmitted to the motion assist robot 200, and the surgical operations such as a moving operation, a pivoting operation, a cutting operation of the robot arms 212, 222, and 232 attached thereto are performed.

For example, the operator 10 may manipulate the robot arms 212, 222, and 232 of the motion assist robot 200, and surgical instruments 211 and 221 or laparoscope 231 connected thereto by using the manipulation member 111. The manipulation member 111 may have various mechanical configurations according to the manipulate method. For example, the manipulation member 111 may be provided in various configurations for operating each of the motion assist robot units 210, 220 and 230 and/or other surgical instruments of the motion assist robot 200, such as a master handle manipulating the motion of each of the motion assist robot units 210, 220 and 230 and various input tools added to the control assist robot 100 for manipulating the functions of the entire system such as joystick, keypad, trackball, touch screen, and foot pedal. Here, the manipulation member 111 is not limited to the shape of a handle, and can be applied without any limitation as long as it can control the operation of the motion assist robot 200 through a network such as a wired or wireless communication network.

In one or more embodiments, voice input or motion input may be applied for user input. That is, the user may wear, on the head thereof, glasses or a head mount display (HMD) with a sensor attached thereto, and the laparoscope 231 may move according to a direction in which the user gazes. Alternatively, when the user makes a command through a voice, such as "left", "right", "first arm", "second arm", etc, the voice command may be recognized and corresponding operations may be performed.

The manipulation member 111 may select at least one of the motion assist robot units 210, 220, and 230, and then control the motion of the selected motion assist robot unit. In an embodiment, at least one of the motion assist robot units 210, 220 and 230 may be selected through an input device (not shown) installed on, for example, the manipulation member 111 or the control assist robot 100. The input device may be buttons, joysticks, keypads, trackballs, touch screens, foot pedals, and the like. Alternatively, voice input or motion input may be used.

In an embodiment, any one of the motion assist robot units 210, 220 and 230 may be selected by a specific movement of the manipulation member 111. For example, any one of the motion assist robot units 210, 220 and 230 may be selected by the motion of shaking the manipulation member 111 up and down or left and right at high speed. In an embodiment, when the manipulation member 111 is shaken once, the first motion assist robot unit 210 may be selected, when the manipulation member 111 is shaken twice, the second motion assist robot unit 220 may be selected, and when the manipulation member 111 is shaken three times, the third motion assist robot unit 230 may be selected. In an embodiment, when the manipulation member 111 is shaken left and right, the first motion assist robot unit 210 may be selected, when the manipulation member 111 is shaken back and forth, the second motion assist robot unit 220 may be selected, and when the manipulation member 111 is shaken up and down, the third motion assist robot unit 230 may be selected. The motion of the manipulating member for selecting the motion assist robot units 210, 220 and 230 described above is an example, and other methods may also be used to select motion assist robot units. For example, as long as distinguished from the normal movements of the manipulation member 111 to control the motions of the motion assist robot units 210, 220 and 230, other movements of the manipulation member 111 may be adopted to select any one of the motion assist robot units 210, 220 and 230.

In an embodiment of the present disclosure, the control assist robot 100 of the laparoscopic surgery system 1 may have low inertia or/and ultra-miniature characteristics. For example, the control assist robot 100 may be developed as an ultra-compact master interface tool with at least one of low inertia (a feature that has less inertia during operation), isotropic (a feature that requires a uniform force depending on the direction of the force), and high intuitiveness to create the same situation as when operating a surgical instrument. In addition, a remote center of motion (RCM) mechanism may be applied so that the manipulation member 111 moves toward a trocar point.

Meanwhile, the laparoscopic surgery system 1 may further include a display member 500, and images captured through the laparoscope 231 may be displayed on the display member 500. Moreover, the display member 500 may display a certain virtual manipulation plate independently or together with the images captured by the laparoscope 231. Here, the display member 500 may include one or more monitors, and information required during the surgery may be independently displayed on each of the monitors.

In an embodiment, the laparoscopic surgery system 1 may include an input device. In the pre-surgery stage, settings required for surgery may be entered with the input device. For example, the surgical site, the type of manual surgery tool the operator will use, the position where the control assist robot 100 is fixed, the information about the operator to perform the surgery (e.g., body information about height, arm length, left-handed or right-handed person, etc., and a professional field, for example, pancreatic laparoscopy specialist, gastric laparoscopy specialist, liver laparoscopy specialist, etc.) may be entered. In an embodiment, the type of manual surgery tools and an optimal one of the motion assist robot units 210, 220 and 230 may be automatically determined according to the input surgery site. In an embodiment, an optimal one of the motion assist robot units 210, 220 and 230 may automatically determined according to the input surgery site and the selected manual surgery tool, or the motion assist robot units 210, 220 and 230 may be displayed on the display 500 or output through audio to allow the operator 10 to select the optimal one. In this case, a combination of surgery parts, manual surgery tools, and the motion assist robot units 210, 220, 230, etc., may be stored as a mapping table in the memory of the laparoscopic surgery system 1, so as to select an optimal combination automatically or suggest the optimal combination to the operator 10. In addition, a method of controlling the motion assist robot 200 by the control assist robot 100 may be determined according to the type of the input manual surgery tool. When the position of the control assist robot 100 is determined, the position where the operator 10 is located is determined. Accordingly, a range in which the motion assist robot 200 is located may be determined. To determine the range in which the motion assist robot 200, the physical dimensions of the operator may be input. In an embodiment, the laparoscopic surgery system 1 may include a memory, a controller device, a processor, or a computer to set and control various devices constituting the laparoscopic surgery system 1. Here, a separate device may be provided to set and control various devices constituting the laparoscopic surgery system 1, or these components may be included in the control assist robot 100 that performs the role of the master robot.

The motion assist robot 200 is arranged at the other side of the bed 400 and may include one or more motion assist robot units 210, 220 and 230. Each of the motion assist robot units 210, 220 and 230 may be provided as a module that may independently move from one another, and an algorithm for preventing collision among the motion assist robot units 210, 220 and 230 may be applied to the laparoscopic surgery system 1. Here, the motion assist robot units 210, 220 and 230 may respectively include robot arms 212, 222, and 232 that move according to the control of the control assist robot 100, and surgical instruments 211 and 221 or the laparoscope 231 coupled to the robot arms 212, 222, and 232.

The motion assist robot units 210, 220 and 230 may respectively include the surgical instruments 211 and 221 having four degrees of freedom (tool_pitch, tool_yaw, tool_roll, and tool_actuation), and the robot arms 212, 222, and 232 having four degrees of freedom (pitch, yaw, roll, and translation) or greater in order to move the surgical instruments 211 and 221 or the laparoscope 231.

Here, the robot arms 212, 222, and 232 may be formed to have a mechanism of a remote center of motion (RCM) structure, by which a pivot (fulcrum) driving may be maintained with respect to an arbitrary movement input of the operator. Here, RCM pivot driving may be implemented by a mechanical structure or an electronic structure.

Meanwhile, as for the surgical instruments 211 and 221, an instrument dedicated to the laparoscopic surgery system 1 according to an embodiment of the present disclosure may be used, or a manual straight type instrument or a manual multi joint instrument may be used. To this end, an adaptor for coupling the straight type instrument may be additionally provided.

As an example, the motion assist robot 200 is disposed at a certain distance from the operator 10, that is, opposite to the operator 10 in the bed 400, and performs a movement in a position where the surgical instrument cannot be deployed at the position of the operator 10. In an embodiment, when the location where the control assist robot is located is input, and the physical dimensions about the operator to perform the surgery, and the type of the manual type instrument 300 to be used are input, a controller device may set an area, in which the manual type instrument 300 of the operator is not deployed, by using the physical dimensions information about the corresponding operator, and may control the motion assist robot units 210, 220 and 230 to operate within the set area. In an embodiment, according to the input surgery site, the manual type instrument 300 which has been selected, and information about the operator, the optimal positions of the motion assist robot units 210, 220 and 230 may be automatically determined by the controller device, or the area in which the motion assist robot units 210, 220 and 230 is able to be positioned may be displayed on the display 500 to allow the operator 10 to select a position thereof.

In general, a robot arm denotes an apparatus having a similar function to that of an arm and/or a wrist of a human being and having a wrist to which a certain tool may be attached. In the present specification, the robot arms 212, 222, and 232 may each be defined as a concept encompassing such elements as an upper arm, a lower arm, a wrist, and an elbow, and a surgical instrument coupled to the wrist, etc. The robot arms 212, 222, and 232 of the motion assist robot 200 as above may be implemented to operate with multi-degree of freedom. The robot arms 212, 222, and 232 may include, for example, the surgical instruments 211 and 221 inserted into a surgical site of the patient, a yaw driving unit for rotating the surgical instruments 211 and 221 in a yaw direction according to the surgical position, a pitch driving unit for rotating the surgical instruments 211 and 221 in a pitch direction that is perpendicular to a rotational driving of the yaw driving unit, a transport driving unit for moving the surgical instruments 211 and 221 in a lengthwise direction thereof, a rotation driving unit for rotating the surgical instruments 211 and 221, and surgical instrument driving unit installed at ends of the surgical instruments 211 and 221 for cutting or incising the surgery lesion. However, the composition of the robot arms 212, 222, and 232 is not limited thereto, and it is to be appreciated that such an example does not limit the scope of claims of the present disclosure. Here, a detailed description of the actual control process, such as rotation and movement of the robot arms 212, 222, and 232 in a corresponding direction by the operator manipulating the manipulation member 110 will be omitted.

The manual type instrument 300 may include various types of manual type instruments such as a straight type instrument with no joint, a multi joint instrument, etc. The operator may directly hold the manual type instrument 300 by hand and perform manual laparoscopic surgery.

In other words, the manual type instrument 300 is directly gripped and driven by the operator, and the surgical instruments 211 and 221 provided in the motion assist robot units 210, 220 and 230 are arranged to be spaced apart from the operator and are remotely controlled by the control assist robot 100.

In addition, one control assist robot 100 is arranged, and a plurality of motion assist robot units 210, 220 and 230 may be arranged. In addition, among the plurality of motion assist robot units, motion assist robot units 210, 220 and 230 to be controlled by the method described above may be selected by the control assist robot 100.

For example, two of the motion assist robot units 210, 220 and 230 may have the surgical instruments 211 and 221 attached thereto, and one of the motion assist robot units 210, 220 and 230 may have the laparoscope 231 attached thereto. In addition, the operator may select the motion assist robot units 210, 220 and 230 to be controlled via the control assist robot 100. As described above, three or more surgical instruments are directly controlled by the operator via one control assist robot 100, and thus, various tools may be controlled accurately and freely according to the intention of the operator without an assistant.

Here, at least the motion assist robot unit 230 on which the laparoscope 231 is installed may be formed to perform the movement through voice manipulation. That is, movements of the laparoscope 231, e.g., moving in upper, lower, left, and right directions, rotation, axis-only rotation, zoom-in/out, returning to basic position, returning to memory position, etc., may not be manipulated when the operator manipulates the control assist robot 100 by hand, but may be performed by recognizing voice command from the operator.

In addition, the laparoscopic surgery system 1 with the assist robot according to the embodiment of the present disclosure may be configured to have a pivot driving mode, in which the surgical instruments 211 and 221 of the motion assist robot 200 operate opposite to the control of the control assist robot 100 based on the trocar point of the patient, and an intuitive driving mode, in which the surgical instruments 211 and 221 of the motion assist robot 200 operate in the same manner as that of the control of the control assist robot 100 based on the trocar point of the patient, and then, switching between the pivot driving mode and the intuitive driving mode may be possible.

For example, in the case of the manual type instrument, the manipulator and the end tool are mirror symmetrical to each other around the trocar point of the patient, so that the movement of the manipulator and the movement of the end tool are opposite to each other. On the contrary, because the surgical robot is electronically controlled, the movements of the manipulator and the end tool in the upper, lower, left, and right directions are identical to each other.

When the operator grips the manual type instrument 300 with one hand and controls the control assist robot 100 with the other hand, the operator may prefer a case in which the motions of the control assist robot 100 and the motion assist robot 200 are opposite to each other such that the movements of both hands are identical to each other, or a case in which the motions of the control assist robot 100 and the motion assist robot 200 are identical to each other such that at least one hand may control intuitively, as necessary. In order to satisfy both needs, the laparoscopic surgery system 1 using the assist robot according to the embodiment of the present disclosure includes both the pivot driving mode and the intuitive driving mode, and then, switching between the pivot driving mode and the intuitive driving mode may be possible. The laparoscopic surgery system 1 may include a switch or button for switching between a pivot driving mode and an intuitive driving mode. Such a switch or button may be located on at least one of the control assist robot 100 and the motion assist robot 200. In an embodiment, the switch or button may be located on or near the manipulation member 111.

Figure 6:
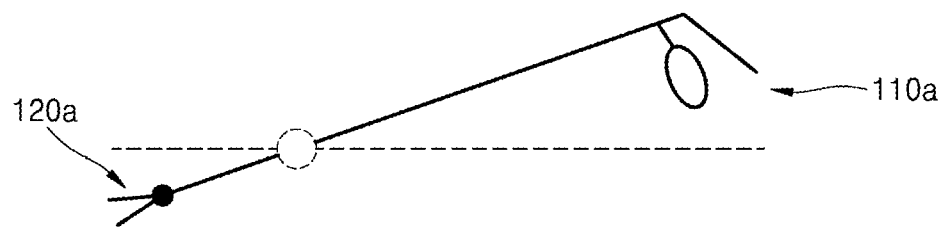
FIG. 6 is an example of a conceptual diagram for explaining the movement of a straight type surgical instrument.

For example, in the case of an example of the surgical instrument shown in FIG. 6, when a manipulator 110a is rotated clockwise around a pivot point (that is, the trocar point), an end tool 120a is also rotated clockwise, when the manipulator 110a is rotated counterclockwise, the end tool 120a is also rotated counterclockwise. In this case, when it comes to upper and lower directions of the operator, when the operator moves the manipulator 110a upward, the end tool 120a is moved downward, and when the operator moves the manipulator 110a downward, the end tool 120a is moved upward. Consequently, the manipulation direction of the operator and the operating direction of the end tool 120a are mirror symmetrical with each other, that is, opposite to each other.

For the operator who is familiar with the straight type surgical instrument, the pivot driving mode may be provided in which movements of the control assist robot 100 and the motion assist robot 200 operate in opposite directions. This mode has the advantage that movement of both hands is consistent, especially when the manual type instrument 300 is the straight type surgical instrument. That is, the pivot driving mode may be a mode, in which the manipulator and an operating unit of both hands are mirror symmetrical with each other and operate in opposite directions.

On the other hand, in the case of a surgery robot (or a multi-joint, multi-degree of freedom hand-held surgical instrument that is intuitively manipulated, created by the present applicant), the user's operation direction and the end tool's operation direction are intuitively identical to each other. A multi-joint, multi-degree of freedom hand-held surgical instrument that is intuitively manipulated is described in U.S. Pat. Nos. 10,722,315 and 10,695,141 of the present applicant, and the contents of these US patents are incorporated by reference).

Figure 7:
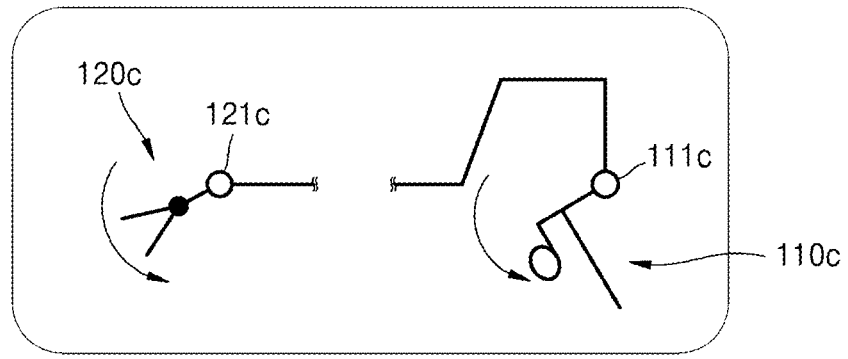
FIG. 7 is a conceptual diagram for explaining the movement of a multi-joint multi-degree of freedom hand-held surgical instrument.

That is, as shown in FIG. 7, when the operator moves a manipulator 110c downward, an end tool 120c also moves downward, and when the operator moves the manipulator 110c to the right, the end tool 120c is also moved to the right.

As described above, for an operator who prefers that the movements of the control assist robot 100 and the motion assist robot 200 are intuitively identical to each other and an intuitive control is possible even with one hand, the intuitive driving mode, in which the control assist robot 100 and the motion assist robot 200 are intuitively moved in the same direction, may be provided. In this mode, the movements of both hands are identical with each other when the manual type instrument 300 is the multi joint multi-degree of freedom hand-held surgical instrument that may be intuitively controlled and developed by the present applicant. That is, the intuitive driving mode may be a mode in which the manipulator and the operating units for both hands are intuitively moved in the same manner. However, when the manual type instrument 300 is the straight type surgical instrument, the movements of both hands are different from each other, so that the operation direction of the operator and the operation direction of the end tool are opposite. On the other hand, when the manual type instrument 300 is the control assist robot 100 and the motion assist robot 200, the operation direction of the operator and the operation direction of the end tool coincide with each other.

A rail 410 may be mounted on the bed 400, and the motion assist robot 200 may be configured to move along the rail 410. That is, the laparoscopic surgery system 1 according to the embodiment of the present disclosure is a modular system in which each of the motion assist robot units 210, 220 and 230 operates individually, and each of the motion assist robot units 210, 220 and 230 should be able to be deployed freely in the optimal position for a corresponding operation. Therefore, the rail 410 is constructed on the bed 400 so that the arrangement in the deployment setting may be freely positioned, and thus, a rail mounting portion on which the motion assist robot units 210, 220 and 230 may be stably fixed on an arbitrary position may be provided.

Figure 8:
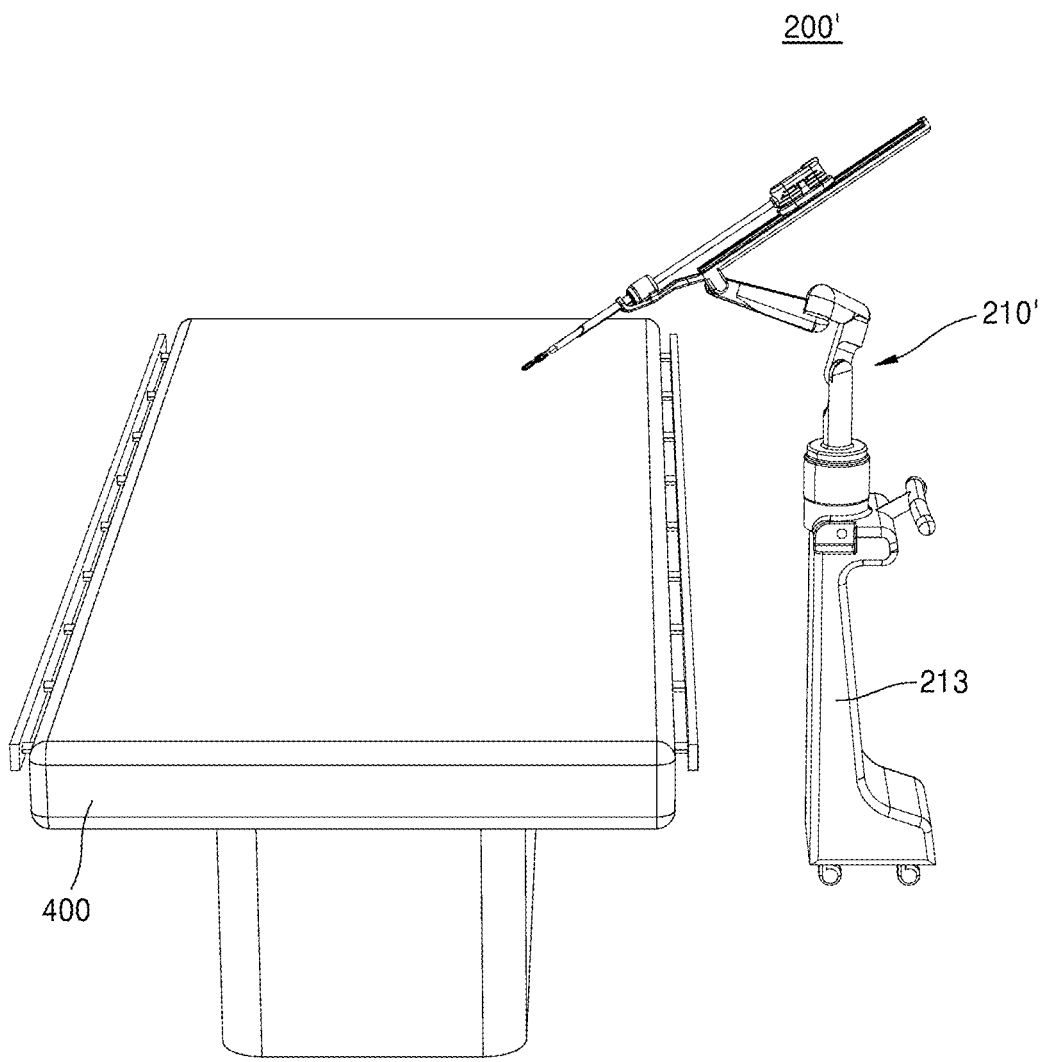
FIG. 8 shows another embodiment of the motion assist robot of the present disclosure.

FIG. 8 shows another embodiment of a motion assist robot 200' of the present disclosure. In this embodiment, the motion assist robot 200' is not directly attached to the bed 400, but may be formed in a separate cart form. In detail, a base 213 acts as a base of an assist robot unit 210'. Here, the base 213 may have a moving device such as a wheel formed on the lower surface thereof, and thus the base 213 may act as a cart. In addition, a position fixing device is further formed on the base 213, so that the position of the base 213 may be fixed during surgery. However, the concept of the present disclosure is not limited thereto, and the base 213 may be formed in such a shape that is detachable from a bed or such a shape that is detachable from a wall surface.

Figure 9:
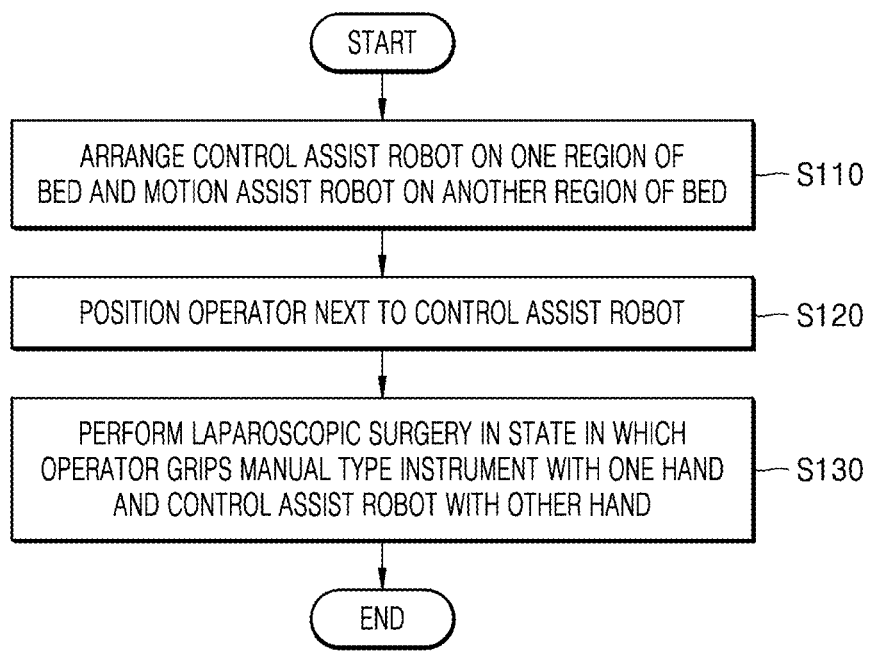
FIG. 9 is a flow chart showing a method of performing laparoscopic surgery using the assist robot of the present disclosure.

FIG. 9 is a flow chart showing a method of performing laparoscopic surgery using the assist robot of the present disclosure.

The method of performing laparoscopic surgery using the assist robot includes arranging the control assist robot 100 on one region of the bed 400 and the motion assist robot 200 on another region of the bed 400 to be spaced a certain distance apart from the control assist robot 100, wherein the motion assist robot 200 includes the surgical instrument 211 that moves according to a control of the control assist robot 100 (S110), positioning the operator next to the control assist robot 100 (S120), and performing laparoscopic surgery in a state in which the operator grips the manual type instrument 300 with one hand and the control assist robot 100 with the other hand (S130).

First, arranging the control assist robot 100 is arranged on one region of the bed 400, and the motion assist robot 200 is arranged on another region of the bed 400 to be spaced the certain distance apart from the control assist robot 100, wherein the motion assist robot 200 includes the surgical instrument 211 that moves according to a control of the control assist robot 100 (S110).

For example, the control assist robot 100 is disposed in one region of the bed 400, and serves to control one or more of the motion assist robots 200. Here, the control assist robot 100 may be formed to have seven or more degrees of freedom in order to control the motion assist robot 200.

The motion assist robot 200 is arranged on another region of the bed 400 and may include one or more motion assist robot units 210, 220 and 230. Each of the motion assist robot units 210, 220 and 230 may include the surgical instruments 211 and 221 or the laparoscope 231 operating according to the control of the control assist robot 100.

Next, the operator is positioned next to the control assist robot 100 (S120).

Next, the laparoscopic surgery is performed in a state in which the operator grips the manual type instrument 300 with one hand and the control assist robot 100 with the other hand (S130). In detail, the manual type instrument 300 is directly gripped and driven by the operator, and the surgical instruments 211 and 221 or the laparoscope 231 provided on the motion assist robot units 210, 220 and 230 are arranged to be spaced apart from the operator and are remotely controlled by the control assist robot 100.

The motion assist robot 200 is disposed at a location spaced a certain distance apart from the operator, that is, an opposite side to the operator on the bed 400, etc., and performs a motion at a location where the operator may not deploy the surgical instrument at his/her position. That is, according to the exemplary embodiment of the present disclosure, in the example of the laparoscopic surgery of FIG. 1, a surgical instrument that was impossible except for a robot may be deployed.

In particular, soft-tissue surgery requires real-time assistant and each movement in the surgery is difficult to be defined in a simple form, unlike other fixed/precise surgery, e.g., orthopedic/neurosurgery. That is, it is important to provide the operator with real-time convenience, rather than static precision assistant, in soft-tissue surgery.

In the case of such soft-tissue surgery, the embodiment of the present disclosure allows the operator to control the motion assist robot while placing the operator next to the operating table. It is differentiated from the surgical robot of a teleoperation platform in which the operator is positioned on a separate non-sterile master robot. And, through this, the operator may adapt to a new platform without a major change in the laparoscopic surgery method as in the example of FIG. 1, the advantages of the laparoscopic surgery (emergency response, etc.) as in the example of FIG. 1, and it may be extended with the robot surgery.

Due to embodiments of the present disclosure, the limitation of the device deployment of the laparoscopic surgery as in the example of FIG. 1 may be overcome. That is, according to the embodiment of the present disclosure, due to the physical limitation of the deployment of the arm of the operator located next to the patient, deployment of the surgical instrument (port configuration), which was impossible unless it was a robot, may be possible, and it may be possible to implement a surgical method that was only possible with the robot. In other words, the motion assist robot is positioned in a position and direction inaccessible to the operator's arm, and the operator manipulates the motion assist robot through the control assist robot, and a surgical method that is impossible in the laparoscopic surgery method as in the example of FIG. 1 may become possible.

Also, the operator may simultaneously control a plurality of instruments, and thus, a surgical ability may be improved and solo-surgery may be possible. That is, the operator controls three or more surgical instruments (two motion assist robots and one camera robot) through one control assist robot, and may manipulate accurately and freely various instruments as intended by the operator without an assistant. In addition, hand movements of the operator may be assisted through compensation for a weight of the surgical instrument for reducing fatigue of the operator due to long-time surgery, hand-shake stabilization, ergonomic arm movement assist, etc.

In addition, since the operator uses the manual laparoscopic surgery instrument with one hand and the assist robot with the other hand, the latest manual type instruments that are not robotized or inexpensive manual type instruments may be used. (On the other hand, in the case of robot surgery where the operator does not need to operate directly in front of the patient, all surgical instruments have to be used as expensive robot-only instruments, so expensive robot-only instruments must be used even for parts that do not require a robot.) Also, even in the robot surgery, the operator may be positioned next to the patient, and thus, the condition of the patient may be checked and an emergency may be dealt with.

FIGS. 10 to 13 are views showing examples of various arrangements of instruments and the operator in various surgeries using the laparoscopic surgery system according to an embodiment of the present disclosure.

According to a kind of surgery, an operator, the control assist robot 100, the motion assist robot 200, and the manual type instrument 300 may be arranged. For example, in surgery for organs located in an upper part of the abdominal cavity (stomach, gallbladder, esophagus, etc.), a lateral part (colon, kidney, spleen, etc.), and a lower part (rectum, appendix, uterus, ovaries, prostate, etc.), it is requested for the operator to be positioned differently and for the instrument to be inserted in different sites. Here, the motion assist robot 200 may include the motion assist robot units 210 and 220 to which the surgical instruments 211 and 221 are coupled, and the motion assist robot unit 230 to which the laparoscope 231 is coupled.

Figure 10:
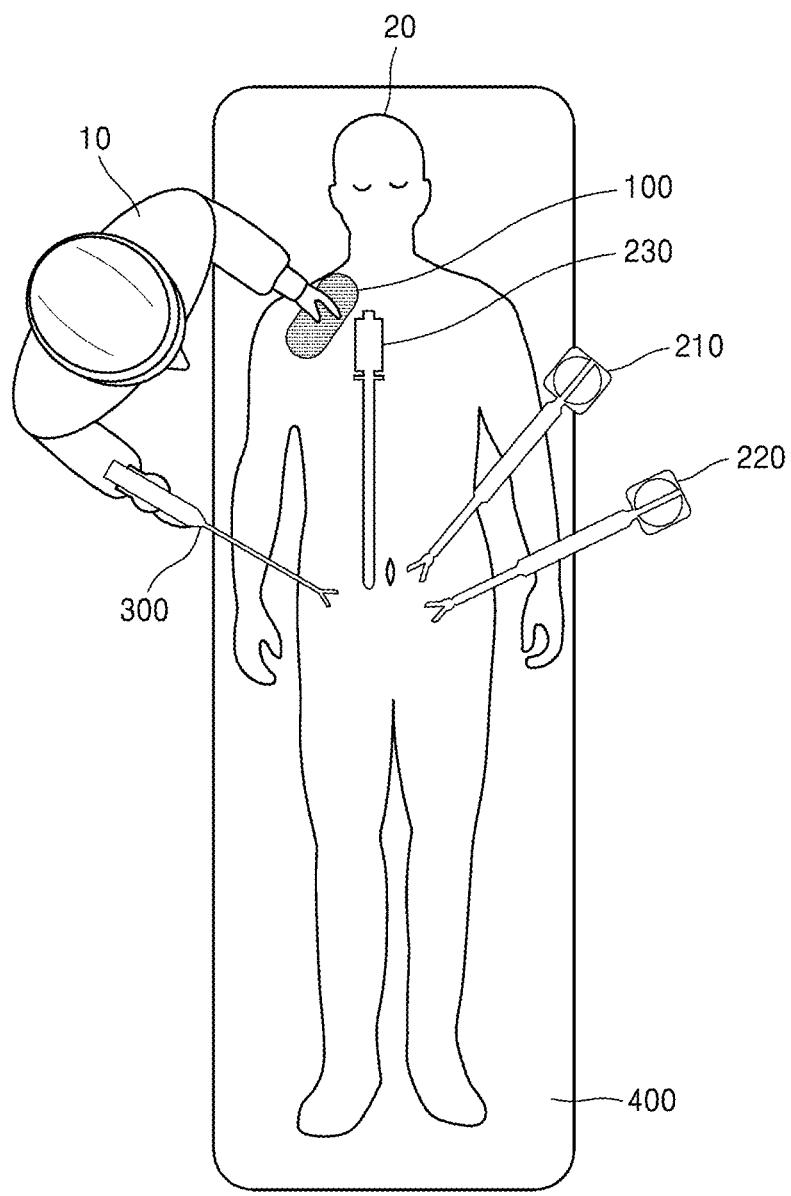
FIGS. 10 to 13 are diagrams showing examples of various arrangements of instruments and an operator in various surgeries using a laparoscopic surgery system in which the operator uses a manual laparoscopic surgical instrument and an assist robot together according to an embodiment of the present disclosure.

In detail, as shown in FIG. 10, when the surgery is performed on an organ located in the lower part of the abdominal cavity, in a state in which the operator is positioned at an upper portion of a side of the patient, the two motion assist robot units 210 and 220 may be arranged at an opposite side to the operator. Alternatively, in a state in which the operator is positioned at a side of the patient, one motion assist robot unit 210 may be arranged at the operator's side and the other motion assist robot unit 220 may be arranged at the opposite side to the operator.

Figure 11:
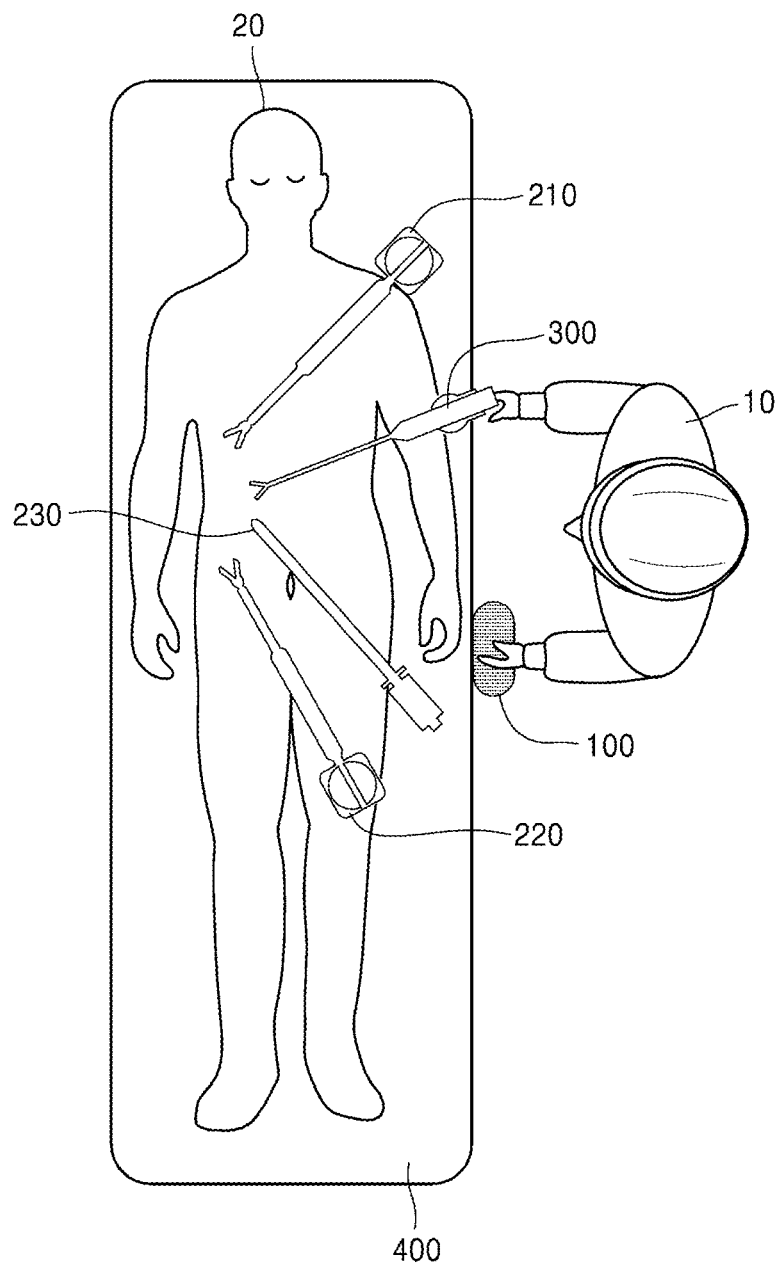

On the other hand, as shown in FIG. 11, when the surgery is performed on an organ located in the side of the abdominal cavity, while the operator is located on the side of the patient, two motion assist robot units 210 and 220 are disposed on the operator's side, two motion assist robot units 210 and 220 may be arranged at a large angle that is difficult to deploy with the operator's arm.

Figure 13:
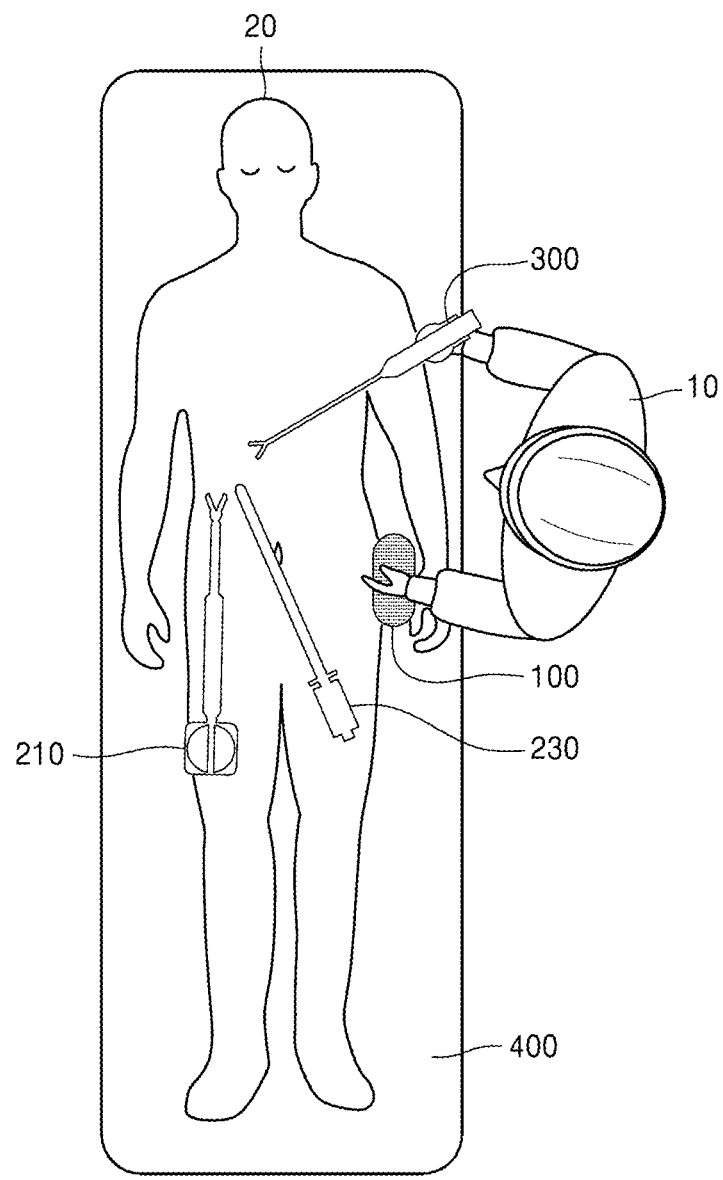

On the other hand, as shown in FIG. 13, when the surgery is performed on an organ located above the abdominal cavity, while the operator is located on the side of the patient, only one motion assist robot unit 210 may be disposed on the opposite side of the operator. Alternatively, in a state in which the operator is positioned at a lower portion of a side of the patient, one motion assist robot unit 210 may be arranged at the operator's side and the other motion assist robot unit 220 may be arranged at the opposite side to the operator. Alternatively, two motion assist robot units 210 and 220 may be disposed on both sides of the patient while the operator is positioned below the patient (that is, the patient's leg side).

Figure 12:
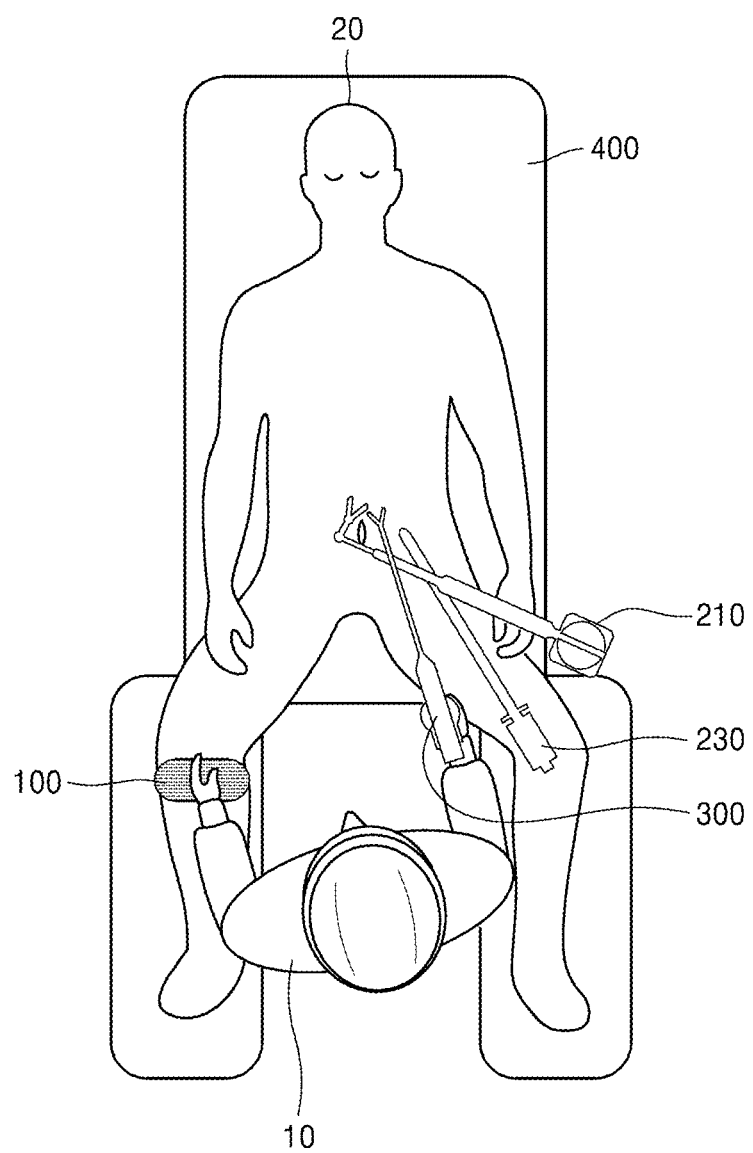

Meanwhile, as shown in FIG. 12, while the operator is located under the patient, instruments may be arranged such that the motion assist robot unit 210, to which the surgical instrument 211 is coupled, the motion assist robot unit 230 to which the laparoscope 231 is coupled, and the manual type instrument 300 may enter the patient's abdominal cavity through a single port.

The arrangement shown in FIGS. 10 to 13 may be applied to the arrangement of instruments and the operator in a specific operation. In the embodiments shown in FIGS. 7 to 13, only the position of the instrument is shown, and a motion assist robot supporting the instrument may be disposed near the position of the instrument. In an embodiment, the robot arm of the motion assist robot has a high degree of freedom (for example, at least 4 degrees of freedom or more), so that various positioning are possible. When a motion assist robot is positioned near each instrument, a robot arm may be positioned like the illustrated instrument.

As an example, when gallbladder resection is operated with multi ports, as shown in FIG. 13, while the operator is positioned on the side of the patient, only one motion assist robot unit 210 may be disposed on the opposite side of the operator.

Meanwhile, when the gallbladder resection is operated with a single port, as shown in FIG. 12, while the operator is located below the patient, instruments may be arranged so that the motion assist robot unit 210 to which the surgical instrument 211 is coupled, the motion assist robot unit 230 to which the laparoscope 231 is coupled and the manual type instrument 300 may entered the abdominal cavity of the patient through the single port.

In addition, when oophorectomy or appendectomy is performed with multi ports, in a state in which the operator is positioned at the side of the patient, only one motion assist robot unit 210 may be arranged at a lower side of the operator.

In addition, when oophorectomy or appendectomy is performed with a single port, in a state in which the operator is positioned at the side of the patient, instruments may be arranged so that the motion assist robot unit 210 to which the surgical instrument 211 is coupled, the motion assist robot unit 230 to which the laparoscope 231 is coupled and the manual type instrument 300 may entered the abdominal cavity of the patient through the single port.

In addition, when nephrectomy is performed with multi ports, as shown in FIG. 11, in a state in which the operator is positioned at a side of the patient, the two motion assist robot units 210 and 220 may be arranged at the operator's side, and the two motion assist robot units 210 and 220 may be arranged at a large angle at which the arms of the operator may not be deployed.

As described above, the present disclosure has been described with reference to various embodiments shown in the drawings, but these are merely exemplary, and those of ordinary skill in the art will understand that various modifications and variations of the embodiments are possible therefrom. Therefore, the scope sought to be protected of the disclosure shall be defined by the appended claims.

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors. As yet another example, in addition to or instead of controlling tilt and/or pan of a camera, roll (or spin) can be controlled. For example, one or more actuators can be provided for controlling the spin.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the present disclosure.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A method of performing a laparoscopic surgery, comprising:

providing a surgical bed on which a patient is placed, a slave assist robot disposed at or adjacent to a first region of the surgical bed, and a master assist robot disposed at or adjacent to a second region of the surgical bed, the second region being apart from the first region, the slave assist robot being configured to move relative to the surgical bed and comprising a base and a robotic arm attached to the base, and the slave assist robot being configured to move at least one laparoscopic surgery instrument attached to the robotic arm, and the master assist robot comprising a control handle configured to control the robotic arm, the master assist robot and the slave assist robot being electrically connected to communicate each other;

providing a manual laparoscopic surgery tool at the second region of the surgical bed;

performing a combined laparoscopic surgery on the patient by controlling the control handle of the master assist robot with one hand of a surgeon positioned at the second region of the surgical bed while controlling the manual laparoscopic surgery tool with the other hand of the surgeon;

operating the slave assist robot and the master assist robot in one of a first operation mode or a second operation mode, each of the first operation mode and the second operation mode causing a positional change on an end tool of the laparoscopic surgery instrument, wherein, in the first operation mode, when the control handle of the master assist robot moves along a first direction, the robotic arm of the slave assist robot moves the end tool of the laparoscopic surgery instrument along a second direction opposite to the first direction, and wherein, in the second operation mode, when the control handle of the master assist robot moves along the first direction, the robotic arm of the slave assist robot moves the end tool of the laparoscopic surgery instrument along the first direction;

switching, during the laparoscopic surgery, from the one of the first operation mode or the second operation mode to the other of the first operation mode or the second operation mode in response to receiving a mode change input;

operating, during the laparoscopic surgery, the slave assist robot and the master assist robot in the other of the first operation mode or the second operation mode;

receiving a set of surgery setting information comprising a type of the manual laparoscopic surgery tool; and in response to the received type of the manual laparoscopic surgery tool, selecting the first operation mode or the second operation mode.

2. The method of claim 1, wherein the first region and the second region are located at the same side of the surgical bed.

3. The method of claim 1, wherein the first region is located at a first side of the surgical bed and the second region is located at a second side of the surgical bed that is different from the first side.

4. The method of claim 1, wherein the first region is located at a first side of the surgical bed and the second region is located at a second side of the surgical bed that is opposite to the first side.

5. The method of claim 1, wherein the first region is located at a first side of the surgical bed and the second region is located at a second side of the surgical bed that is adjacent to and crosses the first side the surgical bed.

6. The method of claim 1, wherein the slave assist robot is separate from the surgical bed and configured to move along at least one side of the surgical bed.

7. The method of claim 1, wherein the surgical bed comprises a rail, the slave assist robot is coupled to the rail, and the slave assist robot is configured to move along the rail.

8. The method of claim 1, wherein at least one of the master assist robot or the slave assist robot is detachably coupled to the respective first or second region of the surgical bed.

9. The method of claim 1, wherein an additional slave assist robot is provided at or adjacent to the second region of the surgical bed and configured to move an additional laparoscopic surgery instrument attached to a robotic arm of the additional slave assist robot, wherein the laparoscopic surgery instrument and the additional laparoscopic surgery instrument are different from each other, and wherein the method further comprises:

receiving a user input regarding at least one of a type of the manual laparoscopic surgery tool or a type of the laparoscopic surgery; and automatically selecting one of the laparoscopic surgery instrument or the additional laparoscopic surgery instrument based on the at least one of the type of the manual laparoscopic surgery tool and or the type of the laparoscopic surgery.

10. The method of claim 1, wherein the slave assist robot comprises a first robot arm and a second robot arm, and the at least one laparoscopic surgery instrument comprises a first laparoscopic surgery instrument attached to the first robot arm and a second laparoscopic surgery instrument attached to the second robot arm, wherein the method further comprises:

performing a first movement of the control handle to select the first robot arm to which the first laparoscopic surgery instrument is attached, and performing a second movement of the control handle different from the first movement to select the second robot arm to which the second laparoscopic surgery instrument is attached.

11. The method of claim 10, wherein the first movement and the second movement of the control handle are different in movement directions from each other.

12. The method of claim 10, wherein the first movement and the second movement of the control handle are different in shaking times from each other.

13. The method of claim 1, wherein controlling the control handle of the master assist robot with the one hand of the surgeon and controlling the manual laparoscopic surgery tool with the other hand of the surgeon are simultaneously performed.

14. The method of claim 1, wherein controlling the control handle of the master assist robot with the one hand of the surgeon and controlling the manual laparoscopic surgery tool with the other hand of the surgeon are sequentially performed.

15. The method of claim 1, wherein the base comprises a cart that is not attached to the surgical bed.

16. The method of claim 1, wherein the master assist robot is attached to the surgical bed.

17. The method of claim 1, wherein the master assist robot is configured to move along a rail of the surgical bed.

18. The method of claim 1, further comprising:

determining a manner of controlling the master assist robot in response to the received type of the manual laparoscopic surgery tool.

19. The method of claim 1, further comprising:

in response to the type of the manual laparoscopic surgery tool being a first type, selecting the first operation mode; or in response to the type of the manual laparoscopic surgery tool being a second type different from the first type, selecting the second operation mode.

20. The method of claim 19, wherein the first type of the manual laparoscopic surgery tool comprises a straight type surgical instrument, and wherein the second type of the manual laparoscopic surgery tool comprises a multi-joint multi-degree of freedom hand-held surgical instrument.

21. The method of claim 1, wherein the manual laparoscopic surgery tool comprises a plurality of manual laparoscopic surgery tools, wherein the slave assist robot comprises a plurality of slave assist robots, and wherein the set of surgery setting information further comprises a surgery location of the patient, a physical characteristic and professional field of an operator performing the laparoscopic surgery, the method further comprising:
- automatically determining one of the plurality of manual laparoscopic surgery tools and one of the plurality of slave assist robots based on the surgery location of the patient.

22. The method of claim 21, further comprising:
- storing a combination of multiple surgery locations, the plurality of manual laparoscopic surgery tools, and the plurality of slave assist robots as a mapping table in a memory; and
- automatically selecting an optimal combination of a manual laparoscopic surgery tool and a slave assist robot, or suggesting the optimal combination to the surgeon.

* * * * *